(12) United States Patent
Zhan et al.

(10) Patent No.: US 12,408,888 B2
(45) Date of Patent: Sep. 9, 2025

(54) DETECTOR RESPONSE CALIBARATION DATA WEIGHT OPTIMIZATION METHOD FOR A PHOTON COUNTING X-RAY IMAGING SYSTEM

(71) Applicant: CANON MEDICAL SYSTEMS CORPORATION, Tochigi (JP)

(72) Inventors: Xiaohui Zhan, Vernon Hills, IL (US); Ruoqiao Zhang, Vernon Hills, IL (US); Ilmar Hein, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 288 days.

(21) Appl. No.: 18/333,051

(22) Filed: Jun. 12, 2023

(65) Prior Publication Data
US 2024/0407749 A1  Dec. 12, 2024

(51) Int. Cl.
*A61B 6/58* (2024.01)
*A61B 6/03* (2006.01)
*A61B 6/42* (2024.01)

(52) U.S. Cl.
CPC .............. *A61B 6/585* (2013.01); *A61B 6/032* (2013.01); *A61B 6/4241* (2013.01)

(58) Field of Classification Search
CPC ....... A61B 6/585; A61B 6/032; A61B 6/4241; G01T 1/1647; G01T 1/17; G01T 1/2985
See application file for complete search history.

(56) References Cited

U.S. PATENT DOCUMENTS

| 2021/0113178 A1 | 4/2021 | Zhou et al. |
| 2022/0296202 A1 | 9/2022 | Zhan et al. |
| 2023/0024679 A1* | 1/2023 | Roessl ...................... G01T 1/24 |

FOREIGN PATENT DOCUMENTS

CN  110389138 A  10/2019

OTHER PUBLICATIONS

Emil Y. Sidky et al., A robust method of x-ray source spectrum estimation from transmission . . ., Journal of Applied Physics 97, 124701 (2005); doi: 10:1063/1.1928312, http:/dx.doi.org/10.1063/1.1928312, 12 pgs.

Xinhui Duan, et al., CT scanner x-ray spectrum estimati from th nsmission measurements Med. Phys. 38 (2), Feb. 2011, © 2011 Am: Assoc. Phys. Med., 5 pgs.

Dannis Dickmann, et al., A count rate-dependent method for spectral distortion correction in photon counting CT. Proc. SPIE 10573, Medical Imaging 2018: Physics of Medical Imaging: 1057311 (Mar. 9, 2010), 1 pg.

\* cited by examiner

*Primary Examiner* — Courtney D Thomas
(74) *Attorney, Agent, or Firm* — Oblon, McClelland, Maier &Neustadt, L.L.P.

(57) ABSTRACT

An X-ray scanner system is provided. The system includes a photon-counting detector, a memory, and processing circuitry. The detector has a plurality of detector pixels in a channel direction. The memory stores a detector response forward model of the photon-counting detector. The detector response forward model is to be used during image reconstruction of an imaging object. The processing circuitry estimates an attenuation profile of the imaging object, determine, with respect to each of the plurality of detector pixels, a set of spatial weights, based on the estimated attenuation profile, and update, based on the determined set of spatial weights, the detector response forward model stored in the memory.

20 Claims, 9 Drawing Sheets

DETECTOR RESPONSE CALIBARATION DATA WEIGHT OPTIMIZATION METHOD FOR A PHOTON COUNTING X-RAY IMAGING SYSTEM

BACKGROUND

Field

The disclosure relates to X-ray imaging systems based on a photon counting detector.

Description of the Related Art

Computed tomography (CT) systems and methods are typically used for medical imaging and diagnosis. CT systems generally create projection images through a subject's body at a series of projection angles. A radiation source, such as an X-ray tube, irradiates the body of the subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector can occur within the detector's time response, a phenomenon called pileup. Left uncorrected, pileup effects distort the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from the scanned object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon-counting CT system, the semiconductor-based detector using direct conversion is designed to resolve the energy of the individual incoming photons and measure multiple energy bin counts for each integration period. However, due to the detection physics in such semiconductor materials (e.g., CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is difficult to accurately model such detector response for a PCD just based on physics or Monte Carlo simulations with a certain modeling of the signal induction process, which determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, and thus the generated spectral images.

Calibration methods have been proposed in the literature to solve similar problems. The general idea is to use multiple transmission measurements of various known path lengths to modify the forward model such that it agrees with the calibration measurements. Some ideas are applied on estimation of the X-ray spectrum in conventional CT (see Sidky et al., Journal of Applied Physics 97 (12), 124701 (2005) and Duan et al., Medical Physics 38 (2), February 2011), and later adopted on photon-counting detectors to estimate the combined system spectral response (see Dickmann et al., Proc. SPIE 10573, Medical Imaging 2018: Physics of Medical Imaging. 1057311 (Mar. 9, 2018)). However, there can be many variations in the detail design and implementation of the calibration method, especially considering the application feasibility in a full third-generation CT geometry.

SUMMARY

Disclosed is an X-ray scanner system including a photon-counting detector, a memory, and processing circuitry. The detector has a plurality of detector pixels in a channel direction. The memory stores a detector response forward model of the photon-counting detector. The detector response forward model is to be used during image reconstruction of an imaging object. The processing circuitry estimates an attenuation profile of the imaging object, determine, with respect to each of the plurality of detector pixels, a set of spatial weights, based on the estimated attenuation profile, and update, based on the determined set of spatial weights, the detector response forward model stored in the memory.

Also disclosed is a method for performing calibration data weight modulation in an X-ray scanner system. The X-ray scanner system includes a photon-counting detector and a memory. The detector has a plurality of detector pixels in a channel direction. The memory stores a detector response forward model of the photon-counting detector, to be used during image reconstruction of an imaging object. The method includes: estimating an attenuation profile of the imaging object; determining, with respect to each of the plurality of detector pixels, a set of spatial weights, based on the estimated attenuation profile; and updating, based on the determined set of spatial weights, the detector response forward model stored in the memory.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the disclosure and embodiments, the reader is directed to the Detailed Description section and corresponding figures of the present disclosure as further discussed below.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

The following disclosure provides many different embodiments, or examples, for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present disclosure can be embodied and viewed in many different ways.

Furthermore, as used herein, the words "a," "an," and the like generally carry a meaning of "one or more," unless stated otherwise.

This disclosure relates to spatial modulation of calibration data weights used in a photon-counting CT scanner system, said CT scanner system comprising one or more X-ray tubes that emit X-ray radiation, and an array of detector pixels for receiving the X-ray radiation propagating through a field of view (FOV) of the CT scanning system. The weight modulation scheme can be applied to both the PCD counting and the spectral forward models.

The weight modulation function can be based on the potential imaging object shape, which is estimated based on a known surrogate object, or calculated based on a low-dose scout scan of the imaging object. The modulated weights can be incorporated into the pre-created PCD detector calibration tables, which will be used to generate the attenuation line-integral or the basis material pathlength sinograms, and reconstruct the counting and spectral images. By modulating the calibration data weight based on the pixel location, according to the potential imaging object pathlength profile, the PCD detector response forward model fitting quality can be improved using limited data samples.

Figure 1:
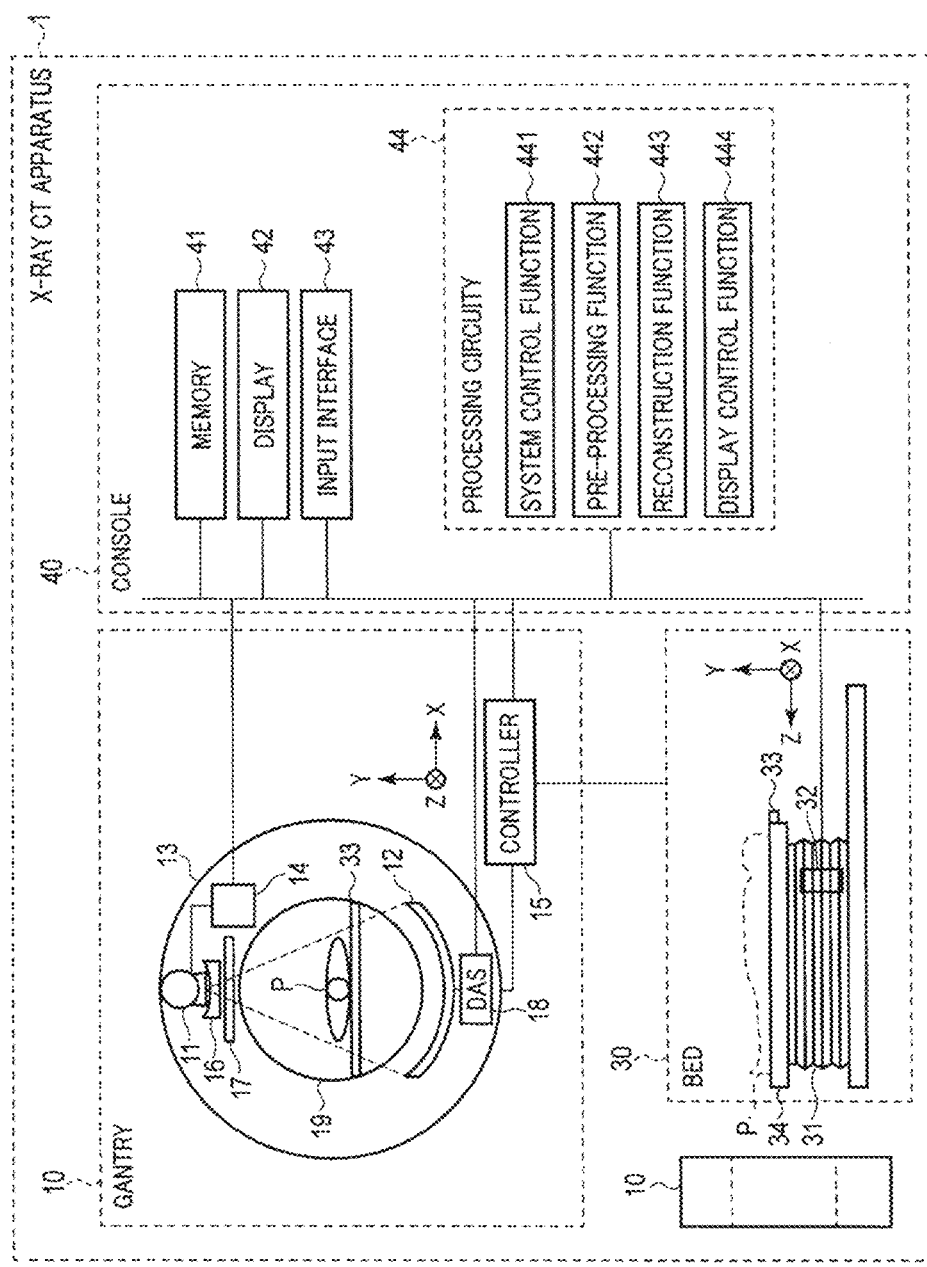
FIG. 1 shows an example of a photon-counting CT scanner system that can incorporate the techniques disclosed herein.

The calibration data weight modulation scheme can be implemented on a photon counting detector included in a photon-counting CT scanning system as described below with reference to FIG. 1. The X-ray CT apparatus 1 shown in FIG. 1 includes a gantry 10, a bed 30, and a console 40 that implements the processing of the medical imaging processing apparatus. For the sake of explanation, FIG. 1 shows multiple gantries 10.

In the present embodiment, the rotation axis of a rotation frame 13 in the non-tilted state, or the longitudinal direction of a table top 33 of the bed 30, is defined as a "Z-axis direction;" the axial direction orthogonal to the Z-axis direction and horizontal to the floor is defined as an "X-axis direction;" and the axial direction orthogonal to the Z-axis direction and vertical to the floor is defined as a "Y-axis direction."

For example, the gantry 10 and the bed 30 are installed in a CT examination room, and the console 40 is installed in a control room adjacent to the CT examination room. The console 40 is not necessarily installed in the control room. For example, the console 40 can be installed together with the gantry 10 and the bed 30 in the same room. In any case, the gantry 10, the bed 30, and the console 40 are communicably connected to one another by wire or radio.

The gantry 10 is a scanner with a configuration for performing X-ray CT imaging on a subject (or an imaging object) P. The gantry 10 includes an X-ray tube 11, an X-ray detector 12, a rotation frame 13, an X-ray high voltage device 14, a controller 15, a wedge filter 16, a collimator 17, and a data acquisition system (DAS) 18.

The X-ray tube 11 is a vacuum tube that generates X-rays by emitting thermal electrons from the cathode (filament) to the anode (target) in response to application of a high voltage and supply of a filament current from the X-ray high voltage device 14. Specifically, X-rays are generated by the thermal electrons colliding with the target. Examples of the X-ray tube 11 include a rotating anode type X-ray tube that generates X-rays by emitting thermal electrons to the rotating anode. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in a channel direction (the X-axis direction, or the column direction) along an arc having a center at the focus of the X-ray tube 11, for example. The X-ray detector 12 has an array structure in which a plurality of X-ray detection element lines, each including a plurality of X-ray detection elements aligned in the channel direction, are aligned in a slice direction (the Z-axis direction, or the row direction).

Specifically, the X-ray detector 12 can be, for example, a direct conversion type detector including a semiconductor element that converts incident X-rays into an electrical signal. The X-ray detector 12 is an example of the PCD according to the present embodiment, and will also be referred to as a "PCD 12."

The rotation frame 13 supports an X-ray generator and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under the control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter (not shown) to a receiver (not shown) arranged on a non-rotating portion (such as the stationary frame, illustration omitted in FIG. 1) of the gantry, and then transferred to the console 40.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator can be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 can be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The CPU can execute a computer program including a set of computer-readable instructions that perform the functions described herein, and the program is stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor and an operating system known to those skilled in the art. Further, the CPU can be implemented as multiple processors cooperatively working in parallel to perform the instructions.

The controller 15 also has the function of performing operation control of the gantry 10 and the bed 30 in response to an input signal from an input interface 43 to be described later attached to the console 40 or the gantry 10. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction, based on tilt angle information input through the input interface 43 attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough, and attenuates the X-rays so that the X-rays emitted from the X-ray tube 11 to the subject P exhibit predetermined distribution. For example, the wedge filter 16 (or bow-tie filter) is a filter obtained by processing aluminum so that it has a predetermined target angle and a predetermined thickness.

The collimator 17 is lead plates or the like for narrowing the application range of X-rays that have passed through the wedge filter 16, and includes a slit formed by combining the lead plates or the like. The collimator 17 may be referred to as an "X-ray diaphragm."

The DAS 18 generates digital data indicating counts of X-rays detected by the X-ray detector 12 (also referred to as "detection data") for each of a plurality of energy bands (referred to as "energy bins" or simply as "bins"). The detection data is a set of a channel number and row number of a source X-ray detection element, a view number indicating a collected view (also referred to as a projection angle), and data of the count value identified by the energy bin number. The DAS 18 is implemented by, for example, an application specific integrated circuit (ASIC) on which a circuit element capable of generating detection data is mounted. The detection data is transferred to the console 40.

The bed 30 is a device to place thereon the subject P to be scanned and move the subject P, and includes a base 31, a bed actuator 32, a table top 33, and a support frame 34.

The base 31 is a case that supports the support frame 34 movably in the vertical direction.

The bed actuator 32 is a motor or actuator that moves the table top 33 on which the subject P is placed in the longitudinal direction of the table top 33. The bed actuator 32 moves the table top 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the table top 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The table top 33 provided on the top surface of the support frame 34 is a plate on which the subject P is placed. The bed actuator 32 may move not only the table top 33 but the support frame 34 in the longitudinal direction of the table top 33.

The console 40 includes a memory 41, a display 42, an input interface 43, and processing circuitry 44. Data communication between the memory 41, the display 42, the input interface 43, and the processing circuitry 44 is performed via a bus. The console 40 is described as being separate from the gantry 10, but the gantry 10 may include the console 40 or part of each constituent element of the console 40.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but a driver that writes and reads various types of information in and from, for example, a portable storage medium such as CD, DVD, or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program according to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate. The display 42 may be provided in the gantry 10. The display 42 may either be a desktop type or configured by a tablet device capable of wirelessly communicating with the console 40.

The input interface 43 receives various types of input operations from the operator, converts a received input operation into an electrical signal, and outputs the electrical signal to the processing circuitry 44. For example, the input interface 43 receives, from the operator, a collection condition for collecting projection data, a reconstruction condition for reconstructing a CT image, and an image-processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44. The input interface 43 may be provided in the gantry 10. The input interface 43 may be configured by a tablet device capable of wirelessly communicating with the console 40.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, and a display control function 444. Each of the functions (the system control function 441, the pre-processing function 442, the reconstruction function 443, and the display control function 444) is not necessarily implemented by a single processing circuit. Processing circuitry can be configured by combining a plurality of independent processors, and the processors can execute respective programs to implement the functions.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43. For example, the system control function 441 obtains a two-dimensional positioning image of the subject P to determine the scan range, imaging condition, etc. The positioning image can also be referred to as a "scanogram" or "scout image."

The pre-processing function 442 generates data obtained by performing pre-processing on detection data output from the DAS 18, such as logarithmic conversion processing, offset correction processing, processing for sensitivity correction between channels, beam hardening correction, and correction for detector calibrations, detector nonlinearities, polar effects, noise balancing, and material decomposition. Data (detection data) before pre-processing and data after pre-processing can be collectively referred to as "projection data." The pre-processing function 442 is an example of the pre-processor.

The reconstruction function 443 generates CT image data by performing reconstruction processing using a filtered back projection method, a successive approximation reconstruction method, a stochastic image reconstruction method, or the like, on the projection data generated by the pre-processing function 442. The reconstruction function 443 is an example of the reconstruction processor. Image filtering, smoothing, volume rendering, or image differential processing can be applied to the CT image data if required. The display control function 444 converts CT image data generated by the reconstruction function 443 into tomographic image data of a given cross section, or three-dimensional image data by a publicly-known method, based on the input operation received from the operator via the input interface 43. The generation of three-dimensional image data can be performed directly by the reconstruction function 443. The display control function 444 is an example of the display controller.

In one implementation, the X-ray tube 11 is a single source emitting a broad spectrum of X-ray energies, and the PCD 12 can use a direct X-ray radiation detectors based on semiconductors, such as cadmium telluride (CdTe), cadmium zinc telluride (CZT), silicon (Si), mercuric iodide (HgI2), and gallium arsenide (GaAs). As mentioned above, semiconductor-based direct X-ray detectors generally have much faster time response than indirect detectors, such as scintillator detectors. The fast time response of direct detectors enables them to resolve individual X-ray detection events, although at the high X-ray fluxes typical in clinical X-ray applications, some pileup of detection events may occur. The energy of a detected X-ray is proportional to the signal generated by the direct detector, and the detection events can be organized into energy bins yielding spectrally resolved X-ray data for spectral CT.

Figure 2:
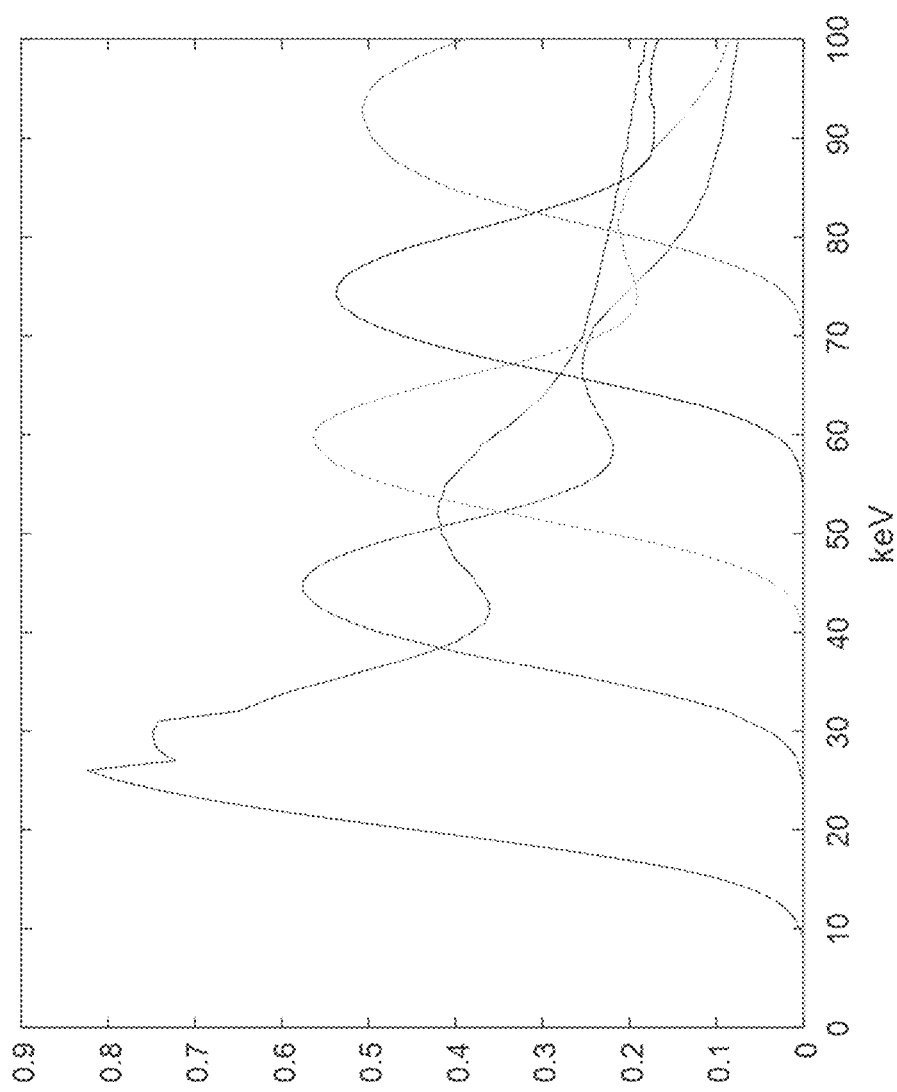
FIG. 2 shows an example of a PCD bin response function Sb (E) for a photon-counting detector, with each curve standing for an exemplary function for an energy bin.

FIG. 2 shows examples of PCD bin response functions. As illustrated in FIG. 2, due to charge sharing, pulse pileup effects, etc., the bin response function has a very broad distribution beyond the ideal bin energy window for each counter. A calibration procedure is typically applied based on multiple transmission measurements of various known attenuation pathlengths to modify the forward model, such that it agrees with the calibration measurements.

For example, when the number of the energy bins is n, the PCD forward model can be given by Equation (1):

$$N_{b,j}(b = 1, \ldots n) = \tag{1}$$
$$\int_{T_b}^{T_{b+1}} \Phi_b(E') \sum_{E_{min}}^{E_{max}} N_{0,j} S_{0,j}(E) D(E, E') e^{\sum_{k=1}^{K} \mu_k(E) l_k} dE dE'$$

$$\Phi_b(E') = \begin{cases} 1, & T_b \leq E' \leq T_{b+1} \\ 0, & \text{others} \end{cases},$$

where E denotes the incident energy, E' denotes the measured energy, $N_{b,j}$ denotes the counts measured at a given detector pixel j for an energy bin b. $\Phi_b(E')$ denotes the binning function which models the function of the DAS 18 (or ASIC), $T_b$ and $T_{b+1}$ are the low and high energy thresholds of the energy bin b, $E_{min}$ and $E_{max}$ are the low and high energy thresholds of the incident spectrum energy range, $N_{0,j}$ is the incident beam spectrum, which can be represented by the air flux measured at the detector pixel j using an air scan, $S_{0,j}(E)D(E,E')$ is the detector response calibration term ("DR"), and $\Sigma_{k=1}^{K} \mu_k(E) l_k$ is the attenuation sample at the detector pixel j.

To calibrate the forward model parameters, a set of slab scans of known materials and thicknesses are collected. Let $N_{b,i,j}$ be the measured count at the detector pixel j for the energy bin b and a slab i (i=1, . . . , m), the parameters in the PCD forward model can be determined by solving the minimization problem using Equation (2):

$$DR_j^* = \operatorname{argmin}_{DR} \sum_{b=1}^{n} \sum_{i=1}^{m} (y_{b,i}(DR_j) - N_{b,i,j})^2 \tag{2}$$

where $y_{b,i}$ is the counts calculated with respect to the energy bin b, the slab i, and the detector pixel j, with $DR_j$ under a certain air flux $N_{0j}$ based on Equation (1).

Note that the above equations are designed for the spectral mode of the photon-counting CT. When the photon-counting CT operates under the counting mode, the calculation can be reduced as below:

$$DR_j^* = \operatorname{argmin}_{DR} \sum_{i=1}^{m} (y_{tot,i}(DR_i) - N_{tot,i,j})^2 \tag{3}$$

where $y_{tot,i} = \Sigma_{b=1}^{n} y_{b,i}$, and $N_{tot,i,j} = \Sigma_{b=1}^{n} N_{p,i,j}$.

Figure 3C:
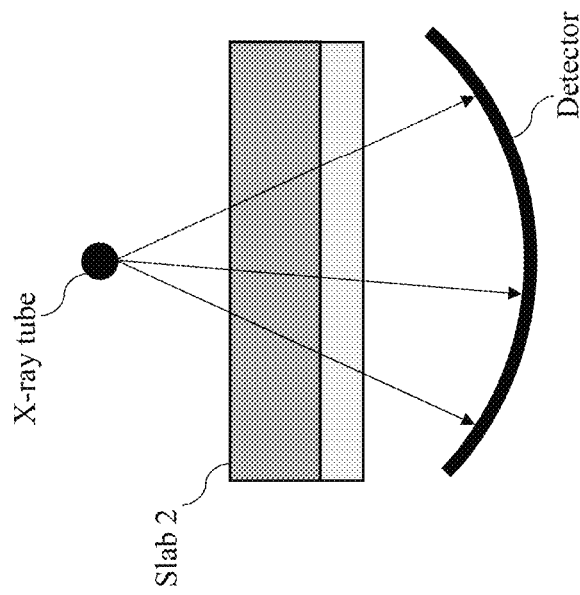
FIGS. 3A-3C show an air scan and slab scans using different combinations of known materials and thicknesses.
Figure 3B:
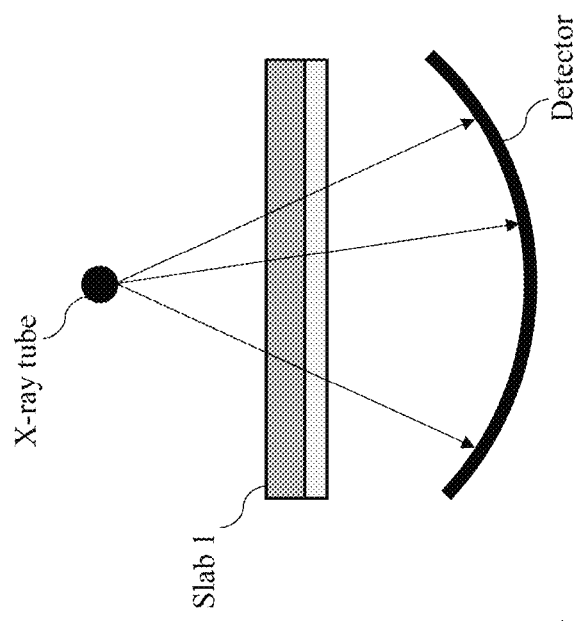
Figure 3A:
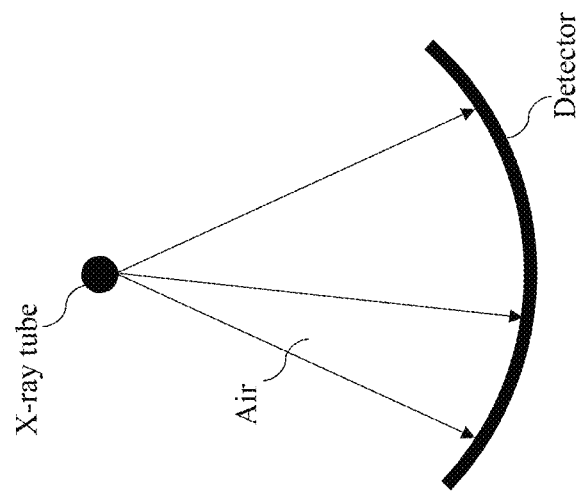

When the PCD calibration scan data is acquired using rectangular slabs 1, . . . , m, the procedure generates a set of measurements with the attenuation samples $att_i = \Sigma_{k=1}^{K} \mu_k l_k$ (i), i=1, . . . , m. FIGS. 3A-3C show the air scan and slab scans using different combinations of known materials and thicknesses. In the example shown in FIGS. 3B-3C, the PCD calibration slab scans utilize two basis materials (i.e., K=2), such as solid water/aluminum, or other similar combinations (e.g., iodine, calcium, etc.), to cover an attenuation phase space that would be encountered in object scans. Each of these data points $N_{b,i,j}$ (for the spectral mode; or $N_{tot,i,j}$ for the counting mode) will be used for the cost function calculation.

When rectangular slabs are used in the slab scans, the set of PCD calibration scan data has nearly the same attenuation samples across the entire detector fan angle. If the weighted least square fit is applied to determine the forward model parameters in the DR function for each pixel, the cost function design usually can weight the measured data based on the statistical noise, which means:

$$\text{cost\_function}_j = \sum_{b=1}^{n} \sum_{i=1}^{m} (y_{b,i}(DR_j) - N_{b,i,j})^2 / \text{Var}(N_{b,i,j}) \tag{4}$$

When the forward model parameterization is sufficient, the above cost function design may work well and generate good calibration results. In the real situation, however, the PCD detector response is usually too complicated so that the parameter fitting quality to all the attenuation samples are not equal, and a natural statistical weight based on Poisson noise is usually not good enough, especially in the high flux region when the pulse pileup effect becomes more severe.

Figure 4:
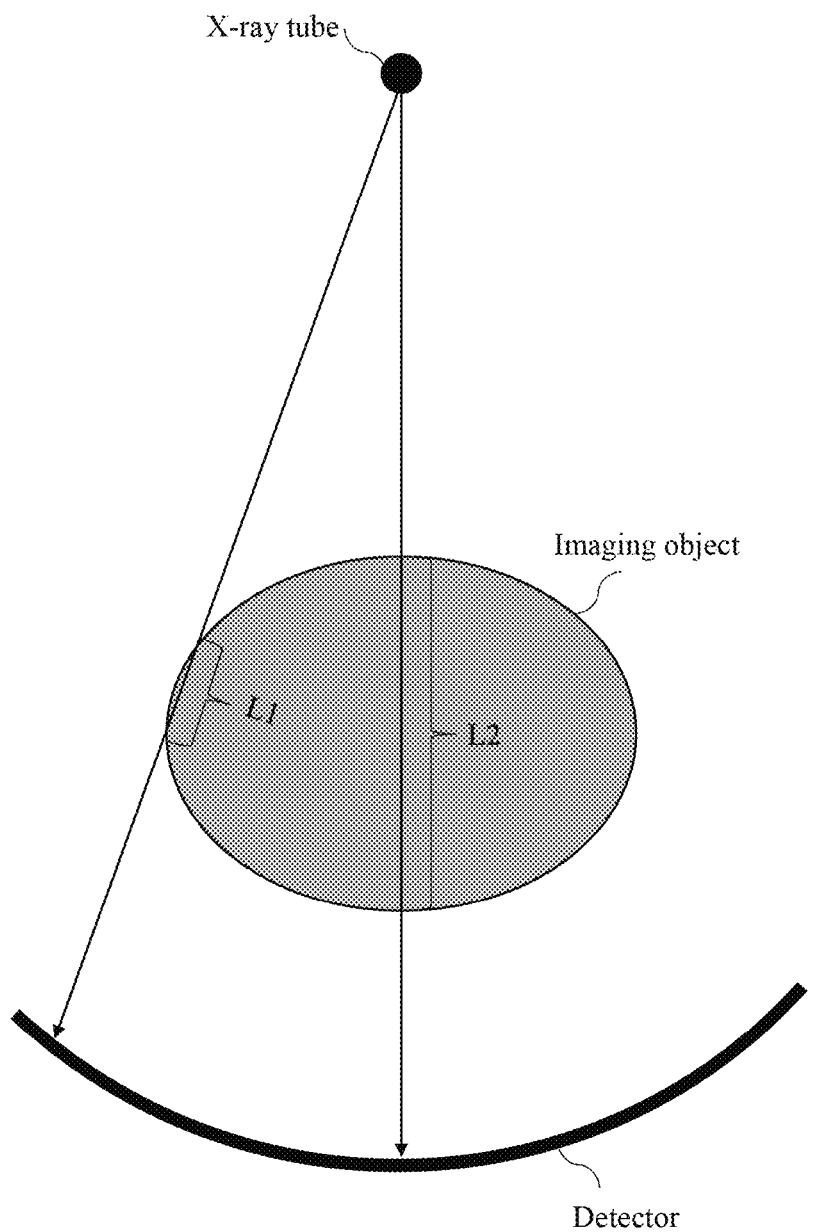
FIG. 4 shows a difference in pathlengths at different fan angles when a scan is performed on an imaging object.

Moreover, the objects scanned by the photon-counting CT typically have a cylindrical shape. While the attenuation in the center of the FOV generally has the largest pathlength, it decreases towards the fan edge and becomes much smaller as it approaches the edge of the imaging object. FIG. 4 shows pathlengths at different fan angles, where the rays at the center region usually would encounter a larger pathlength (e.g., L2) through the scanned object, and the rays at the edge regions encounter a much smaller pathlength (e.g., L1).

Therefore, applying the same weight scheme across the entire detector fan range might not yield optimal fitting quality, leading to suboptimal image quality. Instead, it is desirable to prioritize the fitting quality at large pathlengths over small pathlengths in the center of the fan range, while prioritizing the fitting quality at small pathlengths over large pathlengths towards the fan edges.

Figure 5:
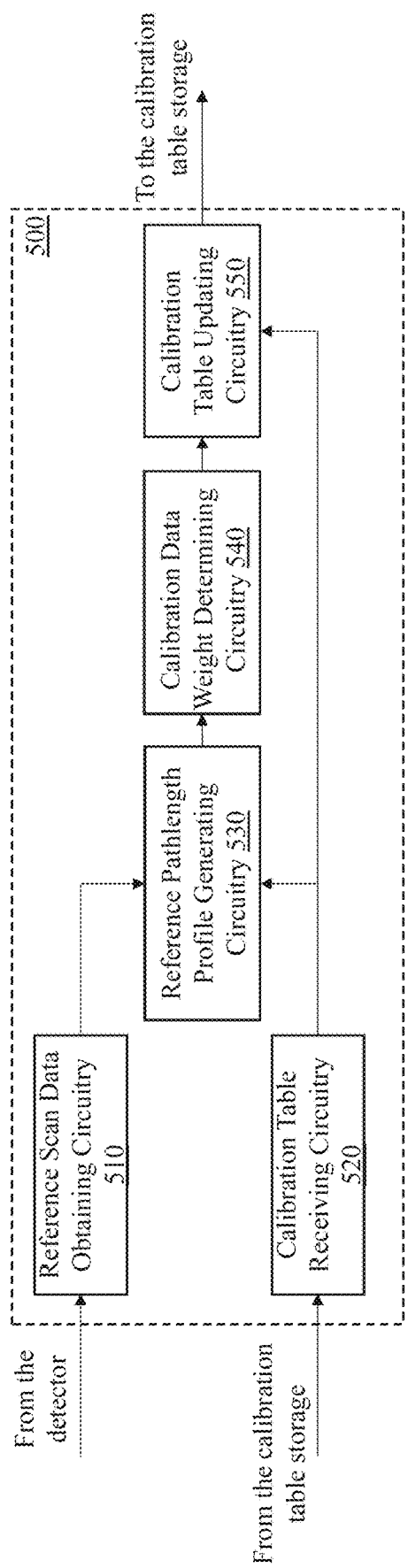
FIG. 5 shows a block diagram of a calibration data weight optimization apparatus 500 according to embodiments of the disclosure.

FIG. 5 shows a block diagram of a calibration data weight optimization apparatus 500 according to embodiments of the disclosure. The apparatus 500 includes reference scan data obtaining circuitry 510, calibration table receiving circuitry 520, reference pathlength profile generating circuitry 530, calibration data weight determining circuitry 540, and calibration table updating circuitry 550.

The reference scan data obtaining circuitry 510 obtains reference scan data from the detector of the CT system. The reference scan data can be obtained using various approaches, such as a 2D scout scan or a 3D scout scan of the imaging object. Alternatively, an appropriate phantom can also be used to obtain the reference scan data.

The calibration table receiving circuitry 520 can receive calibration tables from a calibration table storage (not shown) of the CT system. Typically, the calibration tables can be created by performing slab scans using various combinations of known materials and thicknesses, and subsequently stored in the calibration table storage for use in calibrating the forward model of the CT.

Based on the calibration tables and the reference scan data, the reference pathlength profile generating circuitry 530 generates a reference pathlength profile, which can provide an estimation of the pathlengths that the X-rays will encounter at different pixel positions during a scan of the imaging object.

Based on the generated reference pathlength profile, the calibration data weight determining circuitry 540 determines weights for the slab calibration data. For example, in one embodiment, this weighting scheme is designed to ensure that during the forward model fitting process, the calibration slab scan data will be given varying weights across the detector fan angle, with a greater weight placed on the thick slabs in the center of the detector and a greater weight on the thin slabs towards the periphery.

Based on the determined calibration data weights, the calibration table updating circuitry 550 updates the calibration tables and saves them in the calibration table storage. By implementing suitable spatial modulation of the fitting weights, the more relevant pathlength range can be prioritized for each detector pixel. As a result, the fitting quality of the forward model can be further enhanced for the targeted pathlength range, leading to optimized image quality.

Figure 6:
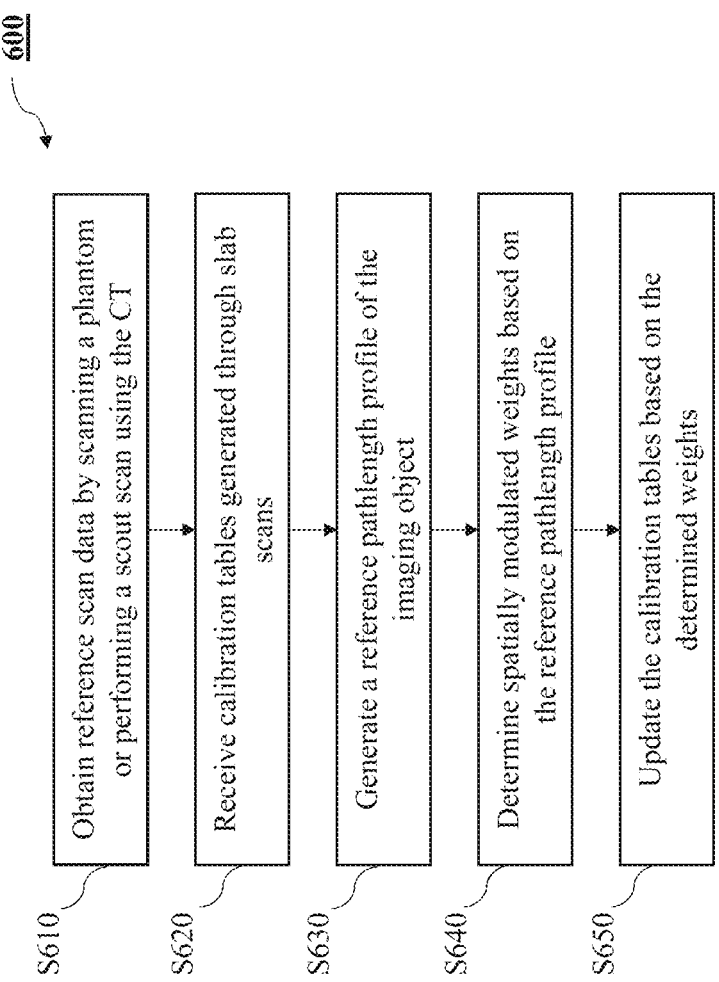
FIG. 6 shows a flow chart of a calibration data weight optimization procedure 600 according to embodiments of the disclosure.

FIG. 6 shows a flow chart of a calibration data weight optimization procedure 600 according to embodiments of the disclosure.

In step S610, reference scan data is obtained. As described above, the reference scan data can be obtained through a scout scan of the imaging object, or by scanning a cylindrical phantom as a surrogate. For example, a 32 cm cylindrical water phantom can be used as the surrogate. Alternatively, a 2D or 3D scout scan of the imaging object can be executed to obtain the reference scan data.

In step S620, calibration tables are received. For example, this step can include retrieving the calibration tables, which can have been prepared previously through a series of slab scans and stored in a calibration table storage.

In step S630, a reference pathlength profile is generated based on the calibration tables and the reference scan data.

For example, when using a water phantom as the surrogate, the reference pathlength profile can either be the water basis material pathlength after material decomposition, or the total water equivalent pathlength at a certain keV. If more than just solid water is used in the slab scans, a certain keV (e.g., 70 keV) can be selected to calculate the total water equivalent pathlength $L_{tot}$ to compare with the reference water phantom profile using the following equation:

$$L_{tot} = L_{water} + L' * \rho' * \frac{\mu'(70 \text{ keV})}{\rho_{water} * \mu_{water}(70 \text{ keV})} \quad (5)$$

If a 2D scout scan (also known as "scano") method is used, the reference pathlength can be generated based on an initial calibration table that assigns an equal weight of $1/\text{Var}(N_{b,i,j})$, for example. The reference water equivalent pathlength across the detector array can be either from maximum values or mean values of the 2D scout scan. If a 3D scout scan is used, the reference water equivalent pathlength can be obtained from the view averaged sinogram.

The scout scan approach can provide additional advantages over the simpler cylindrical phantom approach. By obtaining more information, such as the Z profile of the imaging object, the variations in the body composition and the radiation attenuation across different regions can be taken into account. For example, if significant variances are observed across the entire scanned object, multiple calibration tables can be prepared with different weight modulation schemes, based on the Z profile. This can include applying a first weight scheme to the neck, a second weight scheme to the chest, and a third weight scheme to the abdomen, etc. By tailoring the weight modulation to the specific regions of interest, the detector can achieve more accurate and reliable imaging results.

In step S640, spatially modulated weights can be determined for the slab scan data based on the reference pathlength profile and the calibration tables. More specifically, in the forward model fitting process, the calibration slab scan data can have different data weights across the detector fan angle range. Generally, in the center region of the detector, larger weights can be assigned to thicker slabs, while in the peripheral region of the detector, thin slabs can receive larger weights.

For example, the spatial weight modulation can be designed as a function of the measured slab data $N_{b,i,j}$ and the pixel location $x_j$:

$$w_{bij} = f(N_{b,i,j}, x_j) \quad (6)$$

Therefore, with the adjusted slab data weights, the forward model fitting minimization cost function for the detector pixel j becomes:

$$\text{cost\_function}_j = \sum_{b=1}^{n} \sum_{i=1}^{m} (y_{b,i}(DR_j) - N_{b,i,j})^2 w_{bij} \quad (7)$$

As described above, the weight modulation function can be designed based on predefined imaging object geometry, e.g., a predefined cylindrical phantom. Alternatively, the weight modulation function can be designed on the fly, based on scout scan data of the imaging object. The design of the weight modulation function will be described in detail with reference to different embodiments and FIGS. 7A-7D, 8A-8C, and 9A-9C.

In step S650, the PCD forward model calibration tables are updated for the imaging object by replacing the original weights with the spatially modulated weights. These updated calibration tables can be used later on in the image reconstruction process to produce the counting line-integral or basis material pathlength, for example. By optimizing the calibration data weights based on the imaging object's attenuation profile, a better fitting quality can be achieved utilizing the same limited number of slab data samples. This can lead to an enhanced image quality during the image reconstruction process.

According to one embodiment of the disclosure, for a given detector pixel j, different weight values can be assigned to the slab data samples, based on a comparison of their pathlength to a reference pathlength $L_j$. The reference pathlength can be estimated using the cylindrical phantom or through the scout scan. For all the data samples that have a slab thickness smaller than $L_j$, a first relative weight can be assigned:

$$w1_{b,i,j} = \frac{1}{\text{Var}^{a1}(N_{b,i,j})} \quad (8)$$

If the slab thickness is equal to or larger than $L_j$, the data samples can receive a second relative weight:

$$w2_{b,i,j} = \frac{1}{\text{Var}^{a2}(N_{b,i,j})} \quad (9)$$

By tuning the values of a1 and a2, the relative weights across the slab samples can be adjusted to achieve optimal calibration results. For instance, selecting appropriate values of a1 and a2 can reduce the weight assigned to slab samples with a pathlength much larger (or much smaller, depending on the design requirements) than the reference pathlength. This is because the pathlength of such samples will typically not be encountered during the object scan, and therefore, those sample are less relevant for that pixel.

Typically, the reference pathlength is at its maximum at the center of the detector, and gradually decrease toward the edges. For a detector pixel located at the center of the detector, the weights assigned to all the slab samples can be determined using Equation (8). As the position of the detector pixel moves towards the edge of the detector, more slab samples can receive a weight based on Equation (9). Thus, utilizing Equations (8) or (9), based on the reference pathlength profile, it is possible to achieve spatial weight modulation of the slab data.

If assuming $N_{b,i,j}$ approximately follows Poisson statistics, then its variance will be equal to its expectation (i.e., $\text{Var}(N_{b,i,j})=E(N_{b,i,j})$, and the first and second relative weights become:

$$w1_{b,i,j} = \frac{1}{E^{a1}(N_{b,i,j})} \quad (10)$$

$$w2_{b,i,j} = \frac{1}{E^{a2}(N_{b,i,j})} \quad (11)$$

According to another embodiment of the disclosure, the weight for a given one in the entire set of slab pathlength samples can be designed as:

$$w_{opt}(b, i, j) = \begin{cases} \frac{\text{Var}^{a1}(N_{b,1,j})}{\text{Var}^{a1}(N_{b,i,j})}, & 1 \leq i < I \\ \frac{\text{Var}^{a1}(N_{b,1,j})}{\text{Var}^{a1}(N_{b,I,j})} \times \frac{\text{Var}^{a2}(N_{b,I,j})}{\text{Var}^{a2}(N_{b,i,j})}, & i \geq I \end{cases} \quad (12)$$

where I denotes the highest slab index of which the pathlength is less than the reference pathlength $L_j$.

The values of a1 and a2 can vary from 0 to 5, for example, depending on the details of the PCD forward model and the minimization method. As such, their selection is typically an empirical process that can be done on a case-by-case basis. In an exemplary scenario, a1 is selected as less than a2.

Figure 7A:
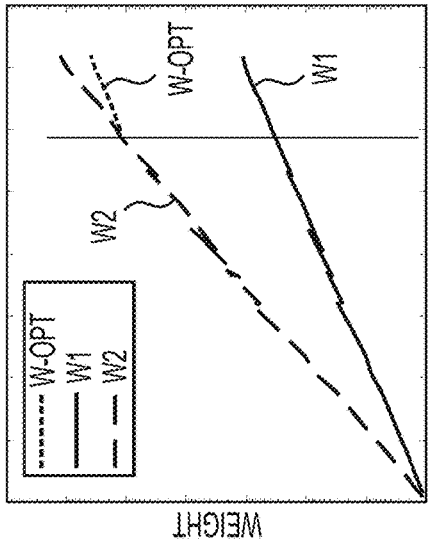
FIGS. 7A-7D show an exemplary weight modulation according to embodiments of the disclosure.
Figure 7B:
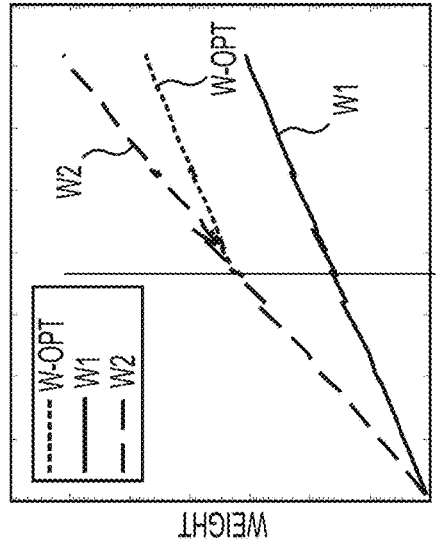
Figure 7C:
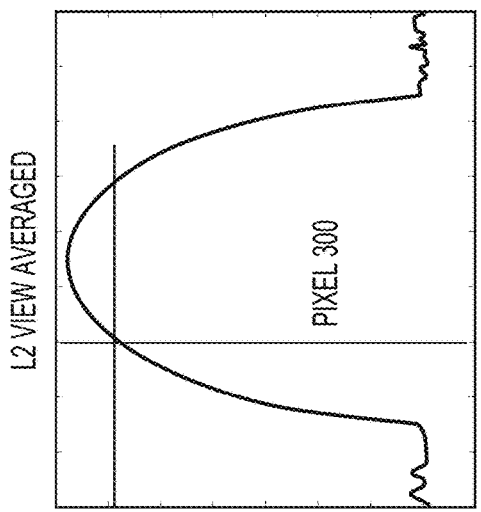

FIGS. 7A-7D illustrate exemplary weight modulation $w_{opt}(b,i,j)$ with a1=1, a2=2. A water basis pathlength view averaged profile is shown in FIGS. 7A and 7C, where the horizontal axis represents the detector pixel positions in the channel direction, and the vertical axis represents the pathlengths (in cm) at the corresponding pixel positions. This pathlength profile is generated using a 32 cm cylindrical water phantom that is placed close to the isocenter.

Figure 7D:
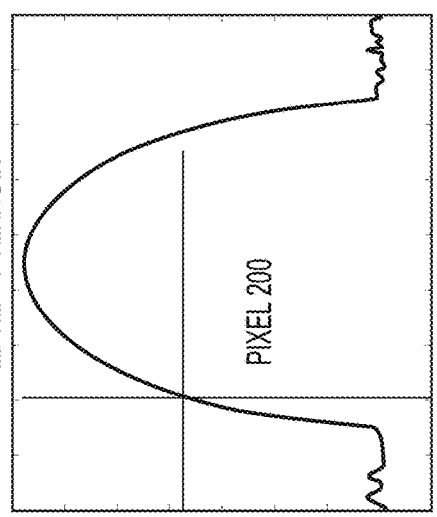

FIGS. 7B and 7D compare three different slab data weights w1, w2, and $w_{opt}$ along the slab sample pathlength, which can be calculated using the above Equations (8), (9), and (10) with a1=1, a2=2. The optimal weight $w_{opt}$ assigned to the detector pixel 300 changes from $$\frac{\text{Var}^{a1}(N_{b,1,j})}{\text{Var}^{a1}(N_{b,i,j})} \text{ to } \frac{\text{Var}^{a1}(N_{b,1,j})}{\text{Var}^{a1}(N_{b,I,j})} \times \frac{\text{Var}^{a2}(N_{b,I,j})}{\text{Var}^{a2}(N_{b,i,j})}$$

when the pathlength reaches the reference pathlength (i.e., 29 cm, as indicated by the water basis pathlength view averaged profile presented in FIG. 7A). Similarly, for detector pixel 200, the switch of the optimal weight $w_{opt}$ occurs when the pathlength reaches the reference pathlength of 17 cm, as observed from the water basis pathlength view averaged profile displayed in FIG. 7C.

For both detector pixels 300 and 200, the weights $w_{opt}$ of the slab samples with a pathlength smaller than the reference pathlength are higher than the weights $$w1\left(=\frac{1}{\text{Var}(N_{b,i,j})}\right).$$

In contrast, the weights $w_{opt}$ of the slab samples with a pathlength equal to or greater than the reference pathlength are lower than the weights $$w2\left(=\frac{1}{\text{Var}^2(N_{b,i,j})}\right).$$

Furthermore, as the reference pathlength increases from the detector pixel 200, which is closer to the edge, to the detector pixel 300, which is closer to the center, more weights are assigned to the slab samples with a large pathlength.

In previous embodiments, the weight modulation function is discrete along the direction of the detector fan angle (or the channel direction), due to the non-contiguous sampling of the attenuation pathlength used in calibration. In another embodiment, the weight modulation function can be designed to be continuous along the detector channel direction.

As an example, a channel-wise windowing function can be applied on top of the original weights, which are derived based on the statistics of slab data. The windowing function can be designed as depending on both pixel location and slab pathlength. For instance, given a slab data point $N_{b,i,j}$ obtained for the energy bin b, the slab i, and the pixel location $x_j$, the original weight $w_{b,i,j}=E^{-a}(N_{b,i,j})$ can be modulated into $w_{opt}(b,i,j)$ through continuous spatial modulation as follows:

$$w_{opt}(b, i, j) = f_{b,i,j} \cdot w_{b,i,j} = f_{b,i,j} \cdot E^{-a}(N_{b,i,j}) \quad (13)$$

The modulation function $f_{b,i,j}$ in Equation (13) can be any arbitrary function that accommodates various optimization criteria and adapts to different scanning conditions. For example, the modulation function can be designed to upweight thick pathlengths for detector channels close to the iso-center, and downweight thick pathlengths for peripheral channels. Similar to previous embodiments, the modulation function $f_{b,i,j}$ can be determined based on a reference pathlength profile that is generated either from a phantom or through a scout scan of the object being scanned.

Figure 8C:
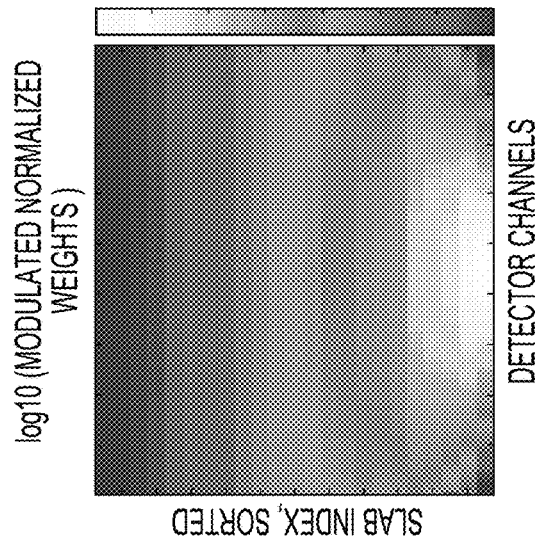
FIGS. 8A-8C show an example of a continuous spatial weight modulation scheme according to one embodiment of the disclosure.
Figure 8B:
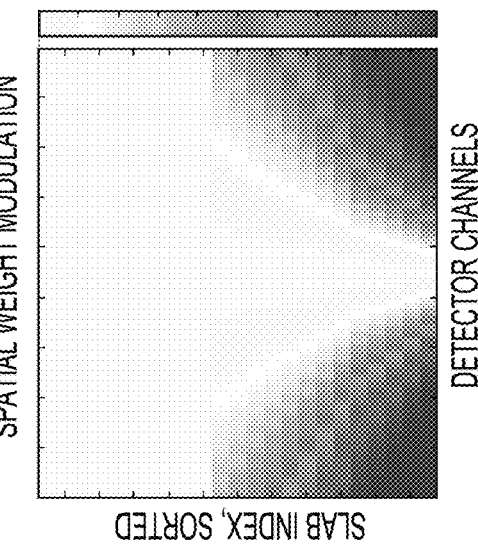
Figure 8A:
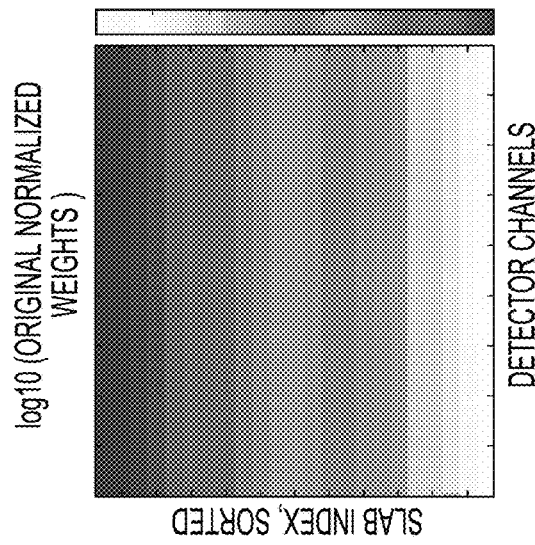

An example of the continuous spatial weight modulation scheme can be seen in FIGS. 8A-8C. One way to generate the spatial modulation is to use Gaussian kernels with different standard deviations σ for different slab pathlengths, for example. More specifically, the standard deviation $\sigma_i$ of the Gaussian kernel can be designed to decrease as the slab pathlength increases. As a result, the weights at thick pathlengths can be gradually suppressed, for peripheral detector channels, by a modulation function as follows:

$$f_{b,i,j} = \exp\{-(j - center_{channel_{index}})^2/\sigma_i^2\} \quad (14)$$

FIGS. 8A and 8C depict normalized weights, before and after the spatial modulation, respectively, for different detector channels and slabs. The original weights shown in FIG. 8A are multiplied by the spatial weight modulation function, illustrated in FIG. 8B, to obtain the modulated weights in FIG. 8C. In each of FIGS. 8A-8C, the center region of the horizontal axis corresponds to the position of the iso-center. As shown in FIG. 8C, the weights are mostly maintained for detector channels close to the iso-center, while for detector channels close to the periphery, the weights for thick slab pathlength are strongly suppressed.

Figure 9C:
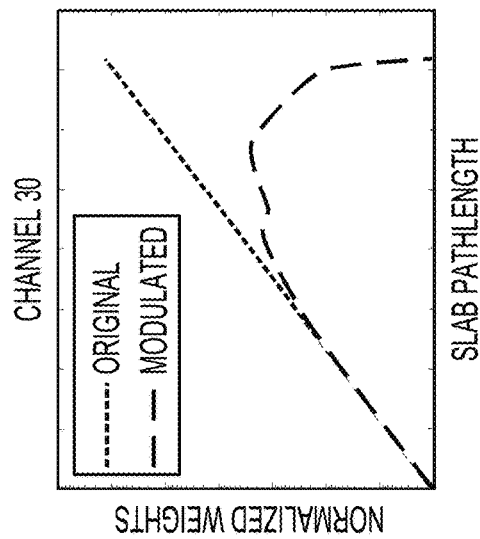
FIGS. 9A-9C show the weights before and after spatial modulation for three exemplary detector channels 400, 200, and 30, according to one embodiment of the disclosure.
Figure 9B:
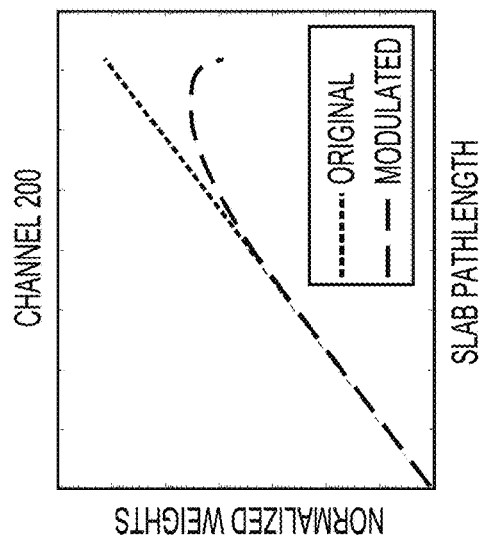
Figure 9A:
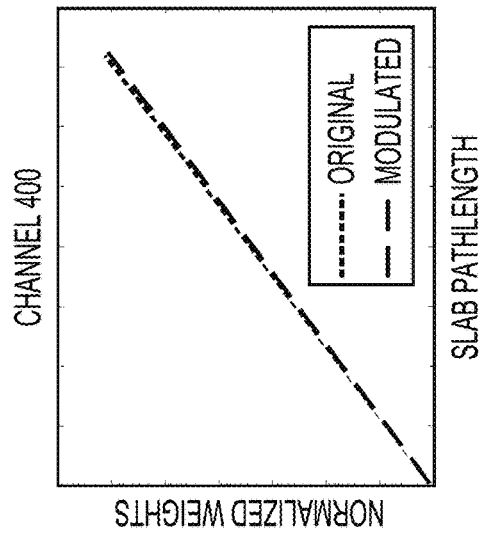

The effect of the spatial modulation function discussed above is demonstrated in a more tangible manner through FIGS. 9A-9C, where the weights before and after modulation are illustrated for three different detector channels 400, 200, and 30. Channel 400 is closest to the iso-center, while channel 200 is somewhat farther away, and channel 30 is the farthest away. The original weights for channel 400 are almost preserved, whereas for channels 200 and 30, which are closer to the periphery, the weights for thick slab pathlengths are significantly reduced.

While the embodiments described above are primarily focused on the spectral mode, they are not limited to that mode. The spatial modulation techniques discussed above can also be applied to the counting mode. For instance, when performing response fitting in the counting mode, the values of $N_{b,i,j}$ in the equations can be replaced with $N_{tot,i,j}$ to represent the total counts above the first energy threshold (e.g., 20 keV), among other modifications as necessary.

Embodiments of the present disclosure may also be as set forth in the following parentheticals.

(1) An X-ray scanner system, comprising: a photon-counting detector having a plurality of detector pixels in a channel direction; a memory storing a detector response forward model of the photon-counting detector, to be used during image reconstruction of an imaging object; and processing circuitry configured to estimate an attenuation profile of the imaging object, determine, with respect to each of the plurality of detector pixels, a set of spatial weights, based on the estimated attenuation profile, and update, based on the determined set of spatial weights, the detector response forward model stored in the memory.

(2) The system of (1), wherein the processing circuitry is further configured to: obtain reference scan data, and generate, as the estimated attenuation profile, a reference pathlength profile based on the obtained reference scan data, the generated reference pathlength profile representing potential attenuation pathlengths to be encountered at the plurality of detector pixels during a scan of the imaging object.

(3) The system of (2), wherein the processing circuitry is further configured to receive calibration data, including data generated through calibration scans using a plurality of slabs, and determine, with respect to each of the plurality of detector pixels, the set of spatial weights based on attenuation pathlengths of the slabs and the reference pathlength profile, and each of the set of spatial weights corresponds to particular calibration data related to one of the plurality of slabs.

(4) The system of (3), wherein the processing circuitry is further configured to use a function to calculate, with respect to each of the plurality of detector pixels, a spatial weight, of the set of spatial weights, corresponding to particular calibration data related to each slab of the plurality of slabs, and the function is dependent on a position of the detector pixel and the particular calibration data related to the slab.

(5) The system of (4), wherein the processing circuitry is further configured to use the function, which includes a modulation term that is dependent on statistics of the calibration data related to the plurality of slabs.

(6) The system of (4), wherein the processing circuitry is further configured to: when the attenuation pathlength of the slab is larger than a value of the reference pathlength profile corresponding to the detector pixel, reduce the spatial weight assigned to the particular calibration data related to the slab.

(7) The system of (2), wherein the processing circuitry is further configured to obtain the reference scan data by using the X-ray scanner system to scan a phantom.

(8) The system of (2), wherein the processing circuitry is further configured to obtain the reference scan data through a 2D or 3D scout scan of the imaging object.

(9) The system of (8), wherein the processing circuitry is further configured to: create a Z-direction profile of the imaging object, and determine, based on the generated Z-direction profile, a plurality of sets of spatial weights, each set of spatial weights corresponding to a different Z-direction region of the imaging object.

(10) The system of (1), wherein the processing circuitry is further configured to scan the imaging object, and reconstruct an image of the imaging object, using the updated detector response forward model.

(11) A method for performing calibration data weight modulation in an X-ray scanner system, the X-ray scanner system including a photon-counting detector and a memory, the detector having a plurality of detector pixels in a channel direction, the memory storing a detector response forward model of the photon-counting detector, to be used during image reconstruction of an imaging object, the method comprising: estimating an attenuation profile of the imaging object; determining, with respect to each of the plurality of detector pixels, a set of spatial weights, based on the estimated attenuation profile; and updating, based on the determined set of spatial weights, the detector response forward model stored in the memory.

(12) The method of (11), wherein the estimating step further comprises: obtaining reference scan data, and generating, as the estimated attenuation profile, a reference pathlength profile based on the obtained reference scan data, the generated reference pathlength profile representing potential attenuation pathlengths to be encountered at the plurality of detector pixels during a scan of the imaging object.

(13) The method of (12), further comprising: receiving calibration data, including data generated through calibration scans using a plurality of slabs, wherein the determining step further comprises determining, with respect to each of the plurality of detector pixels, the set of spatial weights based on attenuation pathlengths of the slabs and the reference pathlength profile, and each of the set of spatial weights corresponds to particular calibration data related to one of the plurality of slabs.

(14) The method of (13), wherein the determining step further comprises using a function to calculate, with respect to each of the plurality of detector pixels, a spatial weight, of the set of spatial weights, corresponding to particular calibration data related to each slab of the plurality of slabs, and the function is dependent on a position of the detector pixel and the particular calibration data related to the slab.

(15) The method of (14), wherein the function includes a modulation term that is dependent on statistics of the calibration data related to the plurality of slabs.

(16) The method of (14), wherein the determining step further comprises: when the attenuation pathlength of the slab is larger than a value of the reference pathlength profile corresponding to the detector pixel, reducing the spatial weight assigned to the particular calibration data related to the slab.

(17) The method of (12), wherein the obtaining step further comprises obtaining the reference scan data by using the X-ray scanner system to scan a phantom.

(18) The method of (12), wherein the obtaining step further comprises obtaining the reference scan data through a 2D or 3D scout scan of the imaging object.

(19) The method of (18), wherein the obtaining step further comprises creating a Z-direction profile of the imaging object, and the determining step further comprises determining, based on the generated Z-direction profile, a plurality of sets of spatial weights, each set of spatial weights corresponding to a different Z-direction region of the imaging object.

(20) The method of 11, further comprises: scanning the imaging object; and reconstructing an image of the imaging object, using the updated detector response forward model.

Numerous modifications and variations of the embodiments presented herein are possible in light of the above teachings. It is therefore to be understood that within the scope of the claims, the disclosure may be practiced otherwise than as specifically described herein.

The invention claimed is:

1. An X-ray scanner system, comprising:
   a photon-counting detector having a plurality of detector pixels in a channel direction;
   a memory storing a detector response forward model of the photon-counting detector, to be used during image reconstruction of an imaging object; and
   processing circuitry configured to
      estimate an attenuation profile of the imaging object,
      determine, with respect to each of the plurality of detector pixels, a set of spatial weights, based on the estimated attenuation profile, and
      update, based on the determined set of spatial weights, the detector response forward model stored in the memory.

2. The system of claim 1, wherein the processing circuitry is further configured to:
   obtain reference scan data, and
   generate, as the estimated attenuation profile, a reference pathlength profile based on the obtained reference scan data, the generated reference pathlength profile representing potential attenuation pathlengths to be encountered at the plurality of detector pixels during a scan of the imaging object.

3. The system of claim 2, wherein
   the processing circuitry is further configured to
      receive calibration data, including data generated through calibration scans using a plurality of slabs, and
      determine, with respect to each of the plurality of detector pixels, the set of spatial weights based on attenuation pathlengths of the slabs and the reference pathlength profile, and
   each of the set of spatial weights corresponds to particular calibration data related to one of the plurality of slabs.

4. The system of claim 3, wherein
   the processing circuitry is further configured to use a function to calculate, with respect to each of the plurality of detector pixels, a spatial weight, of the set of spatial weights, corresponding to particular calibration data related to each slab of the plurality of slabs, and
   the function is dependent on a position of the detector pixel and the particular calibration data related to the slab.

5. The system of claim 4, wherein the processing circuitry is further configured to use the function, which includes a modulation term that is dependent on statistics of the calibration data related to the plurality of slabs.

6. The system of claim 4, wherein the processing circuitry is further configured to:
   when the attenuation pathlength of the slab is larger than a value of the reference pathlength profile corresponding to the detector pixel, reduce the spatial weight assigned to the particular calibration data related to the slab.

7. The system of claim 2, wherein the processing circuitry is further configured to obtain the reference scan data by using the X-ray scanner system to scan a phantom.

8. The system of claim 2, wherein the processing circuitry is further configured to obtain the reference scan data through a 2D or 3D scout scan of the imaging object.

9. The system of claim 8, wherein the processing circuitry is further configured to:
   create a Z-direction profile of the imaging object, and
   determine, based on the generated Z-direction profile, a plurality of sets of spatial weights, each set of spatial weights corresponding to a different Z-direction region of the imaging object.

10. The system of claim 1, wherein the processing circuitry is further configured to
    scan the imaging object, and
    reconstruct an image of the imaging object, using the updated detector response forward model.

11. A method for performing calibration data weight modulation in an X-ray scanner system, the X-ray scanner system including a photon-counting detector and a memory, the detector having a plurality of detector pixels in a channel direction, the memory storing a detector response forward model of the photon-counting detector, to be used during image reconstruction of an imaging object, the method comprising:
    estimating an attenuation profile of the imaging object;
    determining, with respect to each of the plurality of detector pixels, a set of spatial weights, based on the estimated attenuation profile; and
    updating, based on the determined set of spatial weights, the detector response forward model stored in the memory.

12. The method of claim 11, wherein the estimating step further comprises:
    obtaining reference scan data, and
    generating, as the estimated attenuation profile, a reference pathlength profile based on the obtained reference scan data, the generated reference pathlength profile representing potential attenuation pathlengths to be encountered at the plurality of detector pixels during a scan of the imaging object.

13. The method of claim 12, further comprising:
    receiving calibration data, including data generated through calibration scans using a plurality of slabs, wherein the determining step further comprises determining, with respect to each of the plurality of detector pixels, the set of spatial weights based on attenuation pathlengths of the slabs and the reference pathlength profile, and each of the set of spatial weights corresponds to particular calibration data related to one of the plurality of slabs.

14. The method of claim 13, wherein the determining step further comprises using a function to calculate, with respect to each of the plurality of detector pixels, a spatial weight, of the set of spatial weights, corresponding to particular calibration data related to each slab of the plurality of slabs, and the function is dependent on a position of the detector pixel and the particular calibration data related to the slab.

15. The method of claim 14, wherein the function includes a modulation term that is dependent on statistics of the calibration data related to the plurality of slabs.

16. The method of claim 14, wherein the determining step further comprises:

when the attenuation pathlength of the slab is larger than a value of the reference pathlength profile corresponding to the detector pixel, reducing the spatial weight assigned to the particular calibration data related to the slab.

17. The method of claim 12, wherein the obtaining step further comprises obtaining the reference scan data by using the X-ray scanner system to scan a phantom.

18. The method of claim 12, wherein the obtaining step further comprises obtaining the reference scan data through a 2D or 3D scout scan of the imaging object.

19. The method of claim 18, wherein the obtaining step further comprises creating a Z-direction profile of the imaging object, and the determining step further comprises determining, based on the generated Z-direction profile, a plurality of sets of spatial weights, each set of spatial weights corresponding to a different Z-direction region of the imaging object.

20. The method of claim 11, further comprises:

scanning the imaging object; and reconstructing an image of the imaging object, using the updated detector response forward model.

* * * * *